(12) United States Patent
Shu et al.

(10) Patent No.: US 10,472,570 B2
(45) Date of Patent: *Nov. 12, 2019

(54) HIGHLY VERTICAL DIELECTRIC LIQUID CRYSTAL COMPOUND, LIQUID CRYSTAL COMPOSITION, AND LIQUID CRYSTAL DISPLAY DEVICE

(71) Applicant: SHIJIAZHUANG CHENGZHI YONGHUA DISPLAY MATERIAL CO., LTD, Shijiazhuang, Hebei Prov. (CN)

(72) Inventors: Kelun Shu, Shijiazhuang (CN); Guoliang Yun, Shijiazhuang (CN); Yunxia Qiao, Shijiazhuang (CN); Zhengqiang Li, Shijiazhuang (CN)

(73) Assignee: SHIJIAZHUANG CHENGZHI YONGHUA DISPLAY MATERIAL CO., LTD., Shijiazhuang, Hebei Prov (CN)

( * ) Notice: Subject to any disclaimer, the term of this patent is extended or adjusted under 35 U.S.C. 154(b) by 79 days.

This patent is subject to a terminal disclaimer.

(21) Appl. No.: 15/728,729

(22) Filed: Oct. 10, 2017

(65) Prior Publication Data
US 2018/0119012 A1    May 3, 2018

(30) Foreign Application Priority Data
Nov. 2, 2016 (CN) .......................... 2016 1 0948541

(51) Int. Cl.
*G02F 1/1333* (2006.01)
*C09K 19/34* (2006.01)
(Continued)

(52) U.S. Cl.
CPC ........ *C09K 19/3402* (2013.01); *C07C 43/225* (2013.01); *C09K 19/0208* (2013.01);
(Continued)

(58) Field of Classification Search
CPC ............ C09K 19/3402; C09K 19/0208; C09K 19/3066; C09K 19/20; C09K 19/32;
(Continued)

(56) References Cited

U.S. PATENT DOCUMENTS

2018/0094191 A1*    4/2018    Yun ........................ C09K 19/04

\* cited by examiner

*Primary Examiner* — Geraldina Visconti
(74) *Attorney, Agent, or Firm* — Muncy, Geissler, Olds & Lowe, PC

(57) ABSTRACT

Disclosed are a liquid crystal composition comprising a liquid of formula I and formula II-B, and a liquid crystal compound and a related liquid crystal display device

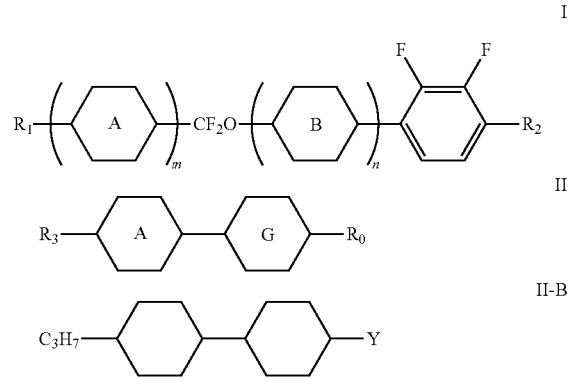

wherein $R_0$, $R_1$, $R_2$ and $R_3$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more non-connected $CH_2$ in $R_0$, $R_1$, $R_2$ and $R_3$ may be substituted with cyclopentyl, cyclobutyl, cyclopropyl or —O—; Y represents ethyl or ethenyl;

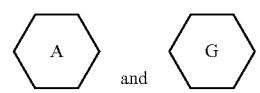

each independently represent one of

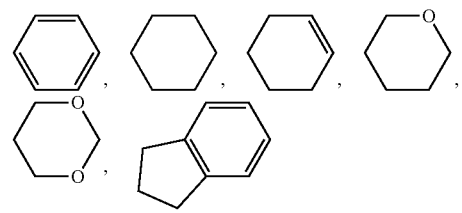

and any fluorobenzene;

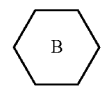

(Continued)

represents benzene or fluorobenzene; and m represents one of 1, 2 and 3, and n represents one of 1 and 0.

12 Claims, No Drawings

(51) Int. Cl.
    *C07C 43/225*     (2006.01)
    *C09K 19/02*     (2006.01)
    *C09K 19/30*     (2006.01)
    *C09K 19/20*     (2006.01)
    *C09K 19/32*     (2006.01)
    *C09K 19/04*     (2006.01)
    *C09K 19/12*     (2006.01)

(52) U.S. Cl.
    CPC .......... *C09K 19/20* (2013.01); *C09K 19/3066* (2013.01); *C09K 19/32* (2013.01); *C09K 2019/0466* (2013.01); *C09K 2019/123* (2013.01); *C09K 2019/301* (2013.01); *C09K 2019/3004* (2013.01); *C09K 2019/3025* (2013.01); *C09K 2019/3422* (2013.01); *C09K 2019/3425* (2013.01)

(58) Field of Classification Search
    CPC .... C09K 2019/0466; C09K 2019/3422; C09K 2019/3425; C09K 2019/123; C09K 2019/3004; C09K 2019/3025; C07C 43/225; G02F 1/1333
    USPC .................................................. 252/299.61
    See application file for complete search history.

HIGHLY VERTICAL DIELECTRIC LIQUID CRYSTAL COMPOUND, LIQUID CRYSTAL COMPOSITION, AND LIQUID CRYSTAL DISPLAY DEVICE

TECHNICAL FIELD

The present invention belongs to the technical field of liquid crystal materials, and more particularly relates to a highly vertical dielectric liquid crystal compound, a liquid crystal composition, and a liquid crystal display device containing such a liquid crystal.

BACKGROUND ART

At present, the expansion of application range of liquid crystal compounds becomes larger and larger, and the liquid crystal compounds can be used in various types of displays, electro-optical devices, sensors and the like. There are a great variety of liquid crystal compounds used in the above-mentioned display field, wherein nematic liquid crystals are used most extensively. Nematic liquid crystals have been used in passive TN and STN matrix displays and systems having a TFT active matrix.

With regard to the application field of thin film transistor techniques (TFT-LCD), although the market in recent years has become very huge, and the techniques also become gradually mature, requirements of display techniques are increasing continuously, especially in terms of achieving a quick response, reducing the drive voltage for reducing power consumption, etc. Liquid crystal materials, as one of the important optoelectronic materials for liquid crystal displays, play an important role in improving the performance of a liquid crystal display.

As liquid crystal materials, they need to have good chemical and thermal stabilities and stabilities to electric fields and electromagnetic radiations. Moreover, as liquid crystal materials used for thin film transistor techniques (TFT-LCD), they not only need to have the stabilities as mentioned above, but also should have properties, such as a broader nematic phase temperature range, a suitable birefringence anisotropy, a very high electrical resistivity, a good ultraviolet resistant property, a high charge retention rate, a low vapor pressure, etc.

For dynamic picture display applications, the elimination of display picture ghosting and trailing requires liquid crystals to have a very quick response speed, and therefore the liquid crystals are required to have a lower rotary viscosity $\gamma_1$; moreover, for portable devices, in order to reduce the device energy consumption, it is desirable for the drive voltage of the liquid crystals to be as low as possible; and for displays for uses such as televisions, the requirements for the drive voltage of the liquid crystals are not as low as that.

The viscosity, in particular rotary viscosity $\gamma_1$, of a liquid crystal compound directly affects the response time after the liquid crystal is energized, and both the rise time ($t_{on}$) and fall time ($t_{off}$) are proportional to the rotary viscosity $\gamma_1$ of the liquid crystal; moreover, since the rise time ($t_{on}$) is related to a liquid crystal cell and the drive voltage, it can be adjusted by means of increasing the drive voltage and reducing the thickness of the liquid crystal cell; while the fall time ($t_{off}$) is irrelevant to the drive voltage, but is mainly related to the elastic constant of the liquid crystal and the thickness of the liquid crystal cell, and thinning of cell thickness can result in a decrease in fall time ($t_{off}$); moreover, in different display modes, the movement manners of liquid crystal molecules are different, and the three modes TN, IPS and VA are inversely proportional to the mean elastic constant K, twist elastic constant and bend elastic constant, respectively.

According to the continuum theory of liquid crystal, a variety of different liquid crystals deformed under the action of an external force (an electric field, a magnetic field) can "rebound" back to the original shapes by intermolecular interactions; likewise, liquid crystals also form a "viscosity" due to the intermolecular force. Small changes of liquid crystal molecules may result in obvious changes in the conventional parameter performance of the liquid crystal, wherein for some of these changes, there is a certain rule, while for some changes, it is difficult to find a rule, which may also have obvious effects on the intermolecular interaction of the liquid crystal, these effects are very subtle, and to date, no perfect theoretical explanation has been formed yet.

The viscosity of a liquid crystal is related to the molecular structure of the liquid crystal, and studying the relationship between the viscosity of a liquid crystal system formed from different liquid crystal molecules and the molecular structures of the liquid crystals is one of important tasks of liquid crystal formulation engineers.

The reason why a liquid crystal display panel has a high energy consumption is that only about 5% of backlight can transmit through a display device and then be captured by human eyes, while most of the light is "wasted". If a liquid crystal having a high light transmittance can be developed, then the backlight intensity can be reduced, thereby achieving the purpose of saving energy consumption and extending the service time of a device.

SUMMARY OF THE INVENTION

The technical problem to be solved by the present invention is to provide a liquid crystal composition having a good stability against light and heat, a lower viscosity, a positive or negative dielectricity, a wider refractive index that may be achieved by adjusting the monomer ratio, and a higher clearing point (a very wide service temperature range), and in particular, the liquid crystal composition has a higher light transmittance, thus allowing a display device to have a higher brightness or an energy saving effect.

The present invention relates to a liquid crystal composition, characterized in that the liquid crystal composition comprises one or more compounds of formula I and one or more compounds of formula II, and said liquid crystal composition at least further comprises one or two compounds of formula II-B included in formula II,

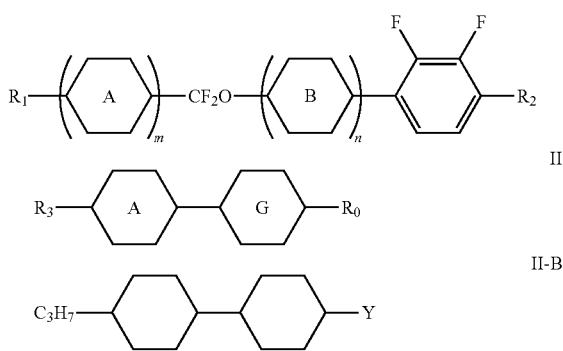

wherein $R_0$, $R_1$, $R_2$ and $R_3$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more non-connected $CH_2$ in $R_0$, $R_1$, $R_2$ and $R_3$ may be substituted with cyclopentyl, cyclobutyl, cyclopropyl or —O—; Y represents ethyl or ethenyl;

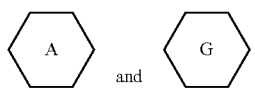

each independently represent one of

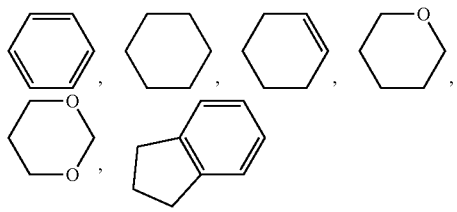

and any fluorobenzene;

represents benzene or fluorobenzene; and m represents one of 1, 2 and 3, and n represents one of 1 and 0.

Said one or more compounds represented by formula I are one or more of compounds represented by formulas I1 to I14; the compounds represented by formula II are one or more of compounds of II1 to II13, II-B-1 and II-B-2; said one or more compounds represented by formula II-B are one or two of compounds represented by formulas II-B-1 and II-B-2,

I1

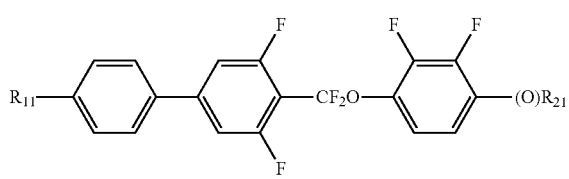

I2

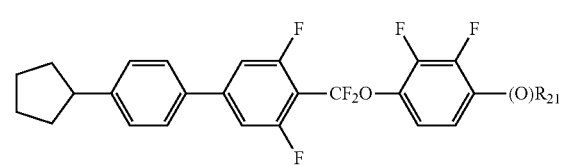

I3

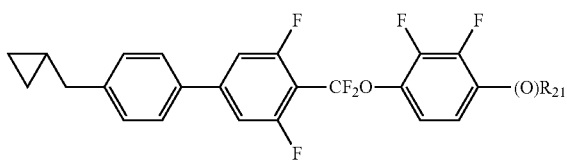

I4

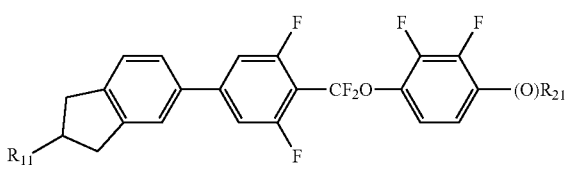

I5

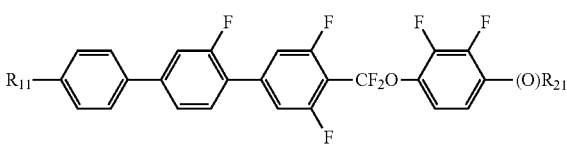

I6

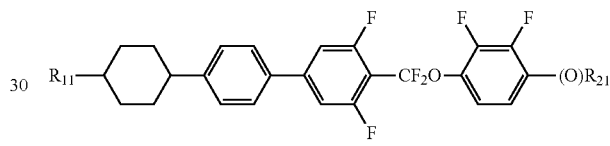

I7

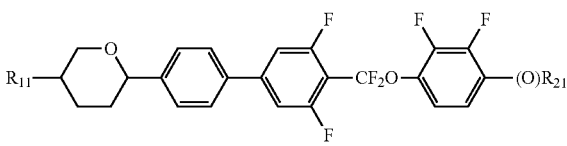

I8

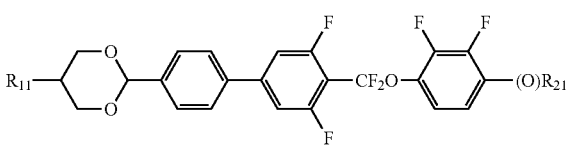

I9

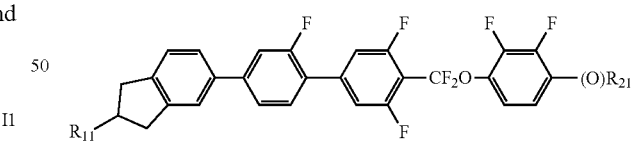

I10

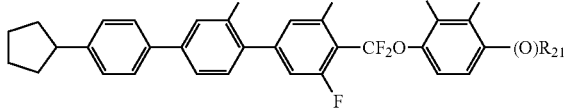

I11

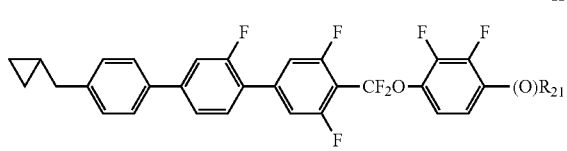

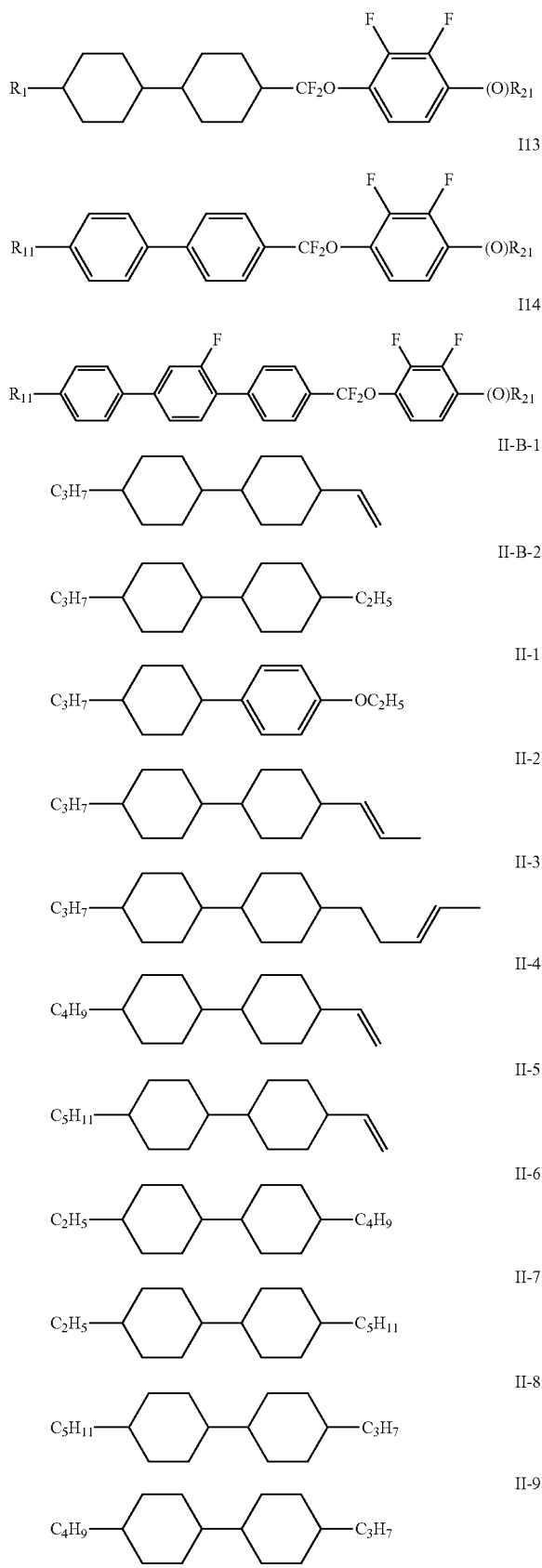
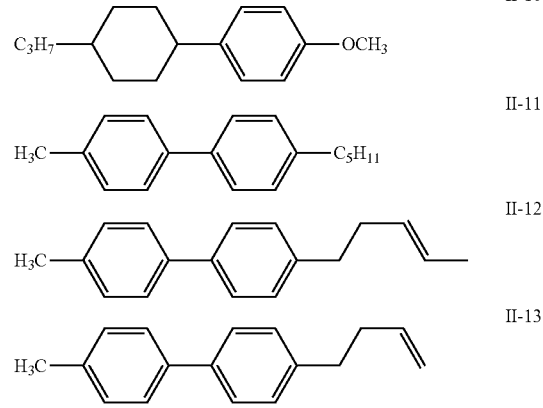

wherein $R_{11}$ represents an alkyl group having a carbon atom number of 1-6, and $R_{21}$ represents an alkyl group having a carbon atom number of 1-5

In the liquid crystal composition of the present invention, the content in mass percentage of the compounds represented by formula I is 0-30%, preferably 5-15%; the content in mass percentage of the compounds represented by formula II-B is 5-60%, preferably 10-45%; and the content in mass percentage of the one or more compounds represented by formula II except the compounds represented by formula II-B is 0-50%, preferably 0-15%.

The compounds represented by formula I have a greater dielectric anisotropy in both the liquid crystal molecule major axis parallel direction and the vertical direction, with the difference (Δε) between the major axis parallel direction dielectric anisotropy and vertical direction dielectric anisotropy being smaller, and these compounds when used in combination with the compounds of formula II have an effect of significantly improving the vertical direction dielectric anisotropy of the mixed liquid crystal without causing the Δε of the mixed liquid crystal; therefore, the addition amount cannot be limited by Δε, so that a greater amount of addition can be achieved. The compounds of formula II, particularly the compounds of formula have a low rotary viscosity, and further have a higher clearing point (CP), and when they are used in combination with compounds represented by formula I, the liquid crystal mixtures have a very low rotary viscosity and a fast response speed.

The liquid crystal mixture of the present invention may be a positive liquid crystal composition, and said liquid crystal composition may further comprise one or more compounds represented by formula III

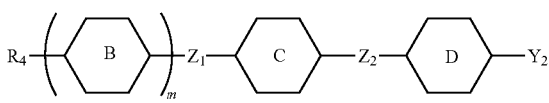

III wherein $R_4$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more $CH_2$ in $R_4$ may be substituted with cyclopentyl, cyclobutyl or cyclopropyl;

each independently represent one of:

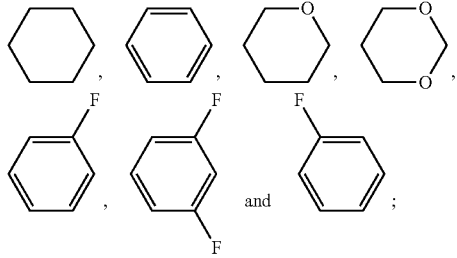

m represents one of 1, 2 and 3; $Z_1$ and $Z_2$ each independently represent a single bond, —CF2O—, —CH2CH2-, or —CH2O—; and $Y_2$ represents F, a fluoro-substituted alkyl group having a carbon atom number of 1-5, a fluoro-substituted alkoxy group having a carbon atom number of 1-5, a fluoro-substituted alkenyl group having a carbon atom number of 2-5, or a fluoro-substituted alkenoxy group having a carbon atom number of 3-8.

Said one or more compounds represented by formula III are compounds of formulas III1 to III22

III1
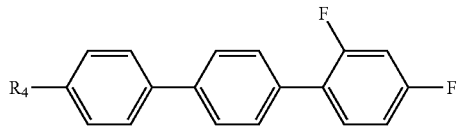

III2
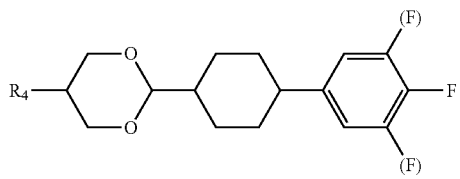

III3
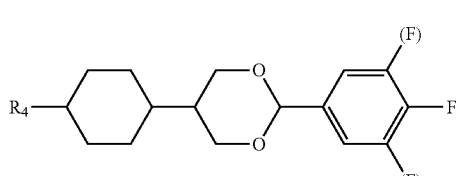

III4
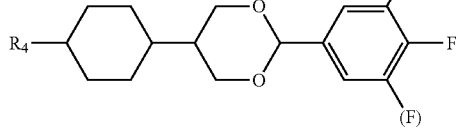

-continued

III5
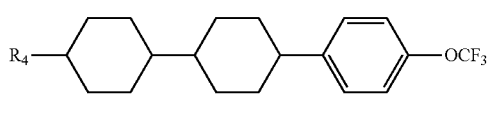

III6

III7
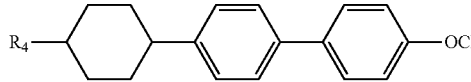

III8

III9
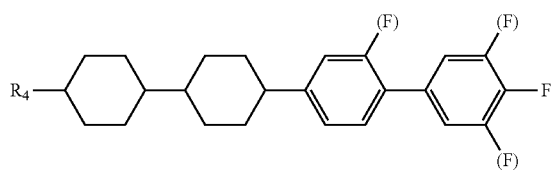

III10
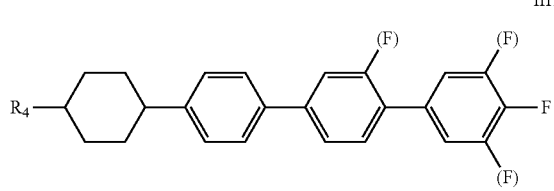

III11

III12
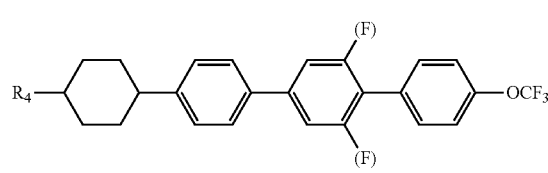

III13
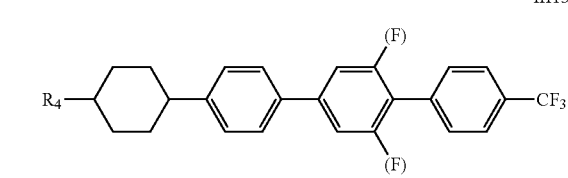

-continued

III14
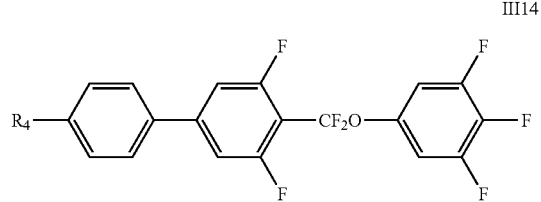

III15
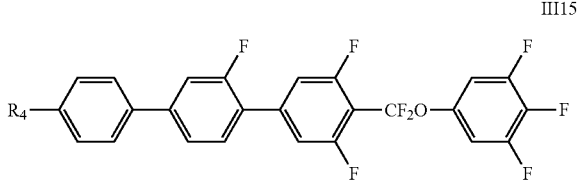

III16
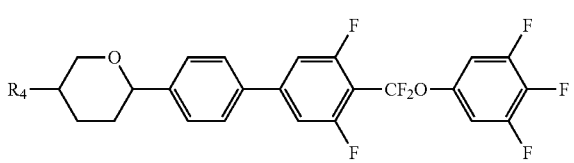

III17
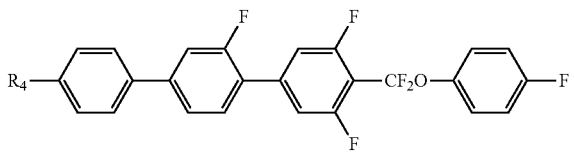

III18
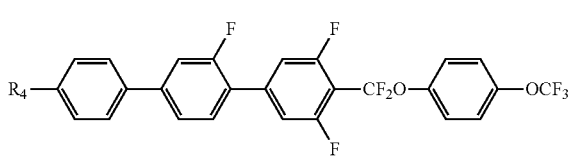

III19
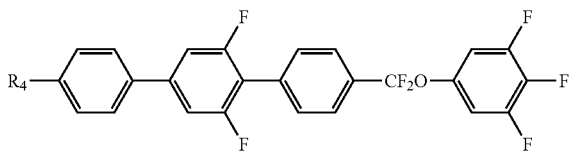

III20
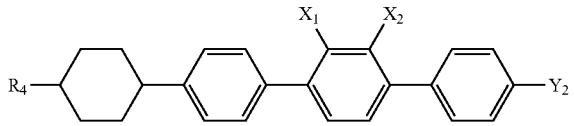

III21
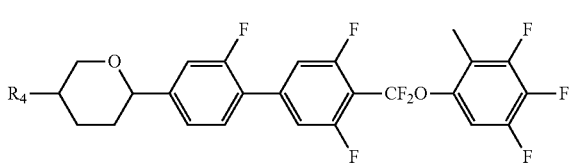

-continued

III22
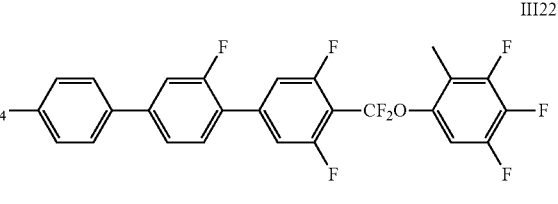

wherein $X_1$ and $X_2$ each independently represent H or F;

wherein $R_4$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in $R_4$ may be substituted with cyclopentyl, cyclobutyl or cyclopropyl; (F) represents H or F.

$Y_2$ represents F, a fluoro-substituted alkyl group having a carbon atom number of 1-5, a fluoro-substituted alkoxy group having a carbon atom number of 1-5, a fluoro-substituted alkenyl group having a carbon atom number of 2-5, or a fluoro-substituted alkenoxy group having a carbon atom number of 3-8.

The compounds represented by the formula III have a greater dielectric anisotropy (Δε), so the addition of an appropriate amount thereof is advantageous to improve the dielectric anisotropy (Δε) of the mixed liquid crystal while reducing the drive voltage of the liquid crystal. They are suitable for use in positive TN, IPS and FFS modes, or may also be suitable for use in PSA-positive TN, IPS and FFS modes.

The compounds of formula II are added in an amount between 0% and 60% and the $CF_2O$ liquid crystals of formula III14-19, III21 and III22 are added in an amount between 0% and 50%, preferably 0% and 30%, mainly for adjusting the dielectric anisotropy and the rotary viscosity, the specific addition amounts being dependent on the requirements of a device with respect to the parameters of the liquid crystals; the tricyclic liquid crystals of III1-9 are added in an amount between 0% and 20%, preferably 0% and 10%; and the tetracyclic liquid crystals of III10-13 and III20 are added in an amount between 0% and 15%, preferably 0% and 10%.

The liquid crystal mixture of the present invention may be a negative liquid crystal composition, and said liquid crystal composition may further comprise one or more compounds represented by formula IV

IV $$R_5 \!-\!\!\left(\!\!\boxed{E}\!\!\right)_{\!\!m}\!\!-\!Z_3\!-\!\!\boxed{\phantom{xx}}\!\!-\!Z_4\!-\!\!\left(\!\!\boxed{F}\!\!\right)_{\!\!n}\!\!-\!R_6$$

wherein $R_5$ and $R_6$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in $R_5$ and $R_6$ may be substituted with cyclopentyl, cyclobutyl or cyclopropyl; $Z_3$ and $Z_4$ each independently represent a single bond, —$CH_2CH_2$— or —$CH_2O$—; and

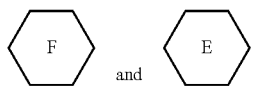

each independently represent one of

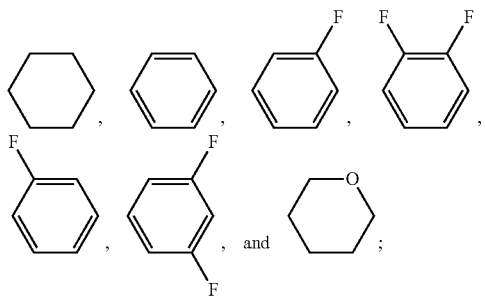

and m represents one of 1, 2 and 3, and n represents one of 0 and 1.

Said one or more compounds represented by formula IV may be one or more of compounds represented by formulae IV1 to IV11

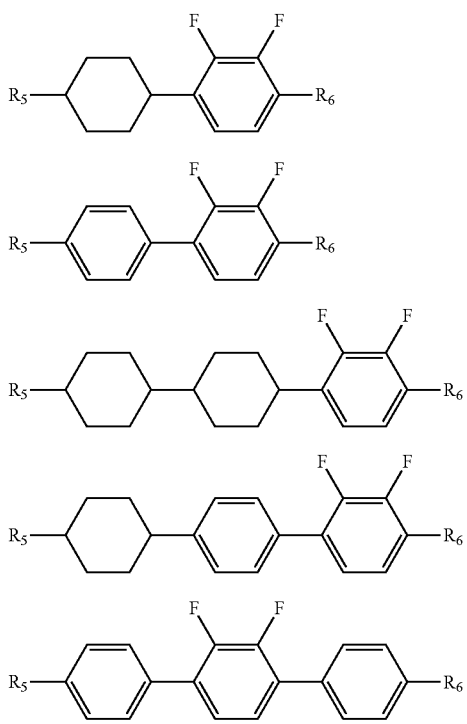

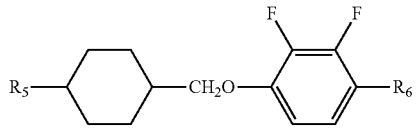

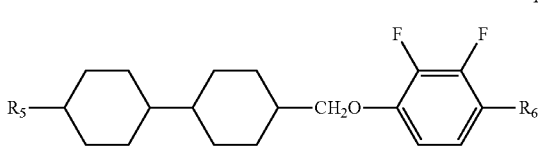

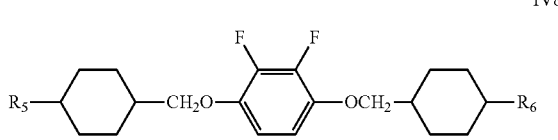

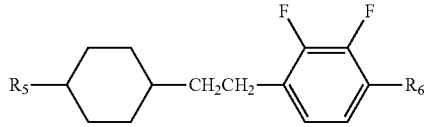

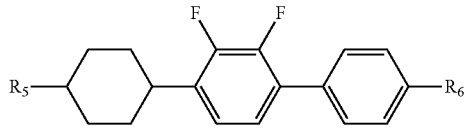

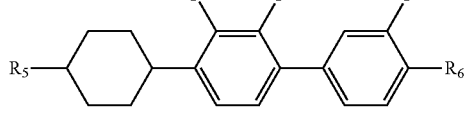

wherein $R_5$ and $R_6$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in $R_5$ and $R_6$ may be substituted with cyclopentyl, cyclobutyl or cyclopropyl.

The compounds represented by the formula IV have a greater negative dielectric anisotropy ($\Delta\varepsilon$), so the addition of an appropriate amount thereof is advantageous to improve the dielectric anisotropy ($\Delta\varepsilon$) of the mixed liquid crystal while reducing the drive voltage of the liquid crystal. They are suitable for use in negative IPS and FFS modes, or may also be suitable for use in PSA-negative VA, IPS and FFS modes.

The compounds represented by formula IV are added in an amount between 0% and 60%, the tricyclic single monomer is added in an amount of generally 10% or less and the bicyclic single monomer is added in an amount that may reach 10% or greater, without the occurrence of precipitation for 20 days at a low temperature of −30° C., the specific addition amounts are dependent on the requirements of a device with respect to the parameters of the liquid crystals.

The liquid crystal mixture of the present invention may be a negative liquid crystal composition, and said liquid crystal composition may further comprise one or more compounds represented by formula V

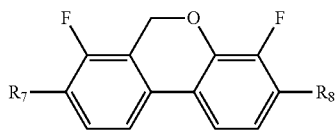
V wherein $R_7$ and $R_8$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in $R_5$ and $R_6$ may be substituted with cyclopentyl, cyclobutyl or cyclopropyl.

The compounds of formula V are preferably triether compounds of V1 and V2,

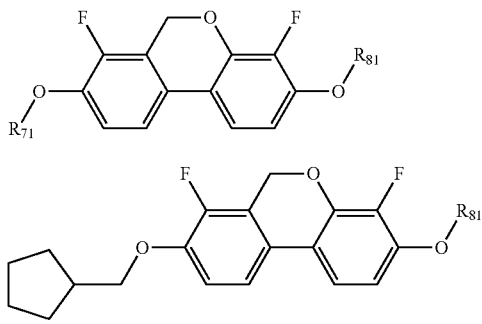

V-1

V-2

The compounds of formula V have a greater dielectric anisotropy ($\Delta\epsilon$), and in particular, the triether compounds of V1 and V2 have a dielectric anisotropy of −10 or greater, which is very advantageous for lower liquid crystal drive voltage.

The liquid crystal mixture of the present invention may be a negative liquid crystal composition, or may also be a positive liquid crystal composition, wherein the liquid crystal mixture may further comprise a compound of formula VI

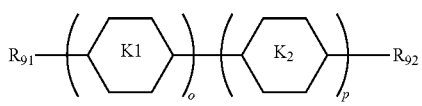
VI wherein $R_{91}$ represents an alkyl group having a carbon atom number of 1-5 or an alkenyl group having a carbon atom number of 2-5; and $R_{92}$ represents an alkyl group having a carbon atom number of 1-5, an alkoxy group having a carbon atom number of 1-5, or an alkenyl group having a carbon atom number of 2-5, and any $CH_2$ in $R_{91}$ and $R_{92}$ may be substituted with cyclopentyl, cyclobutyl or cyclopropyl. o and p represent one of 1 and 2.

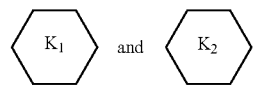

each independently represent one of

and any fluorobenzene;

The compounds of formula VI have a very small dielectric anisotropy ($\Delta\epsilon$), and are generally suitable for adjusting the elastic constant, clearing point CP, refractive index of a mixed liquid crystal.

The compounds of formula VI are preferably the compounds of VI1-1:

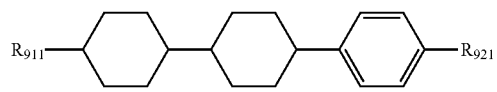
VI1

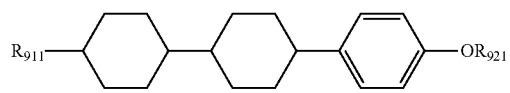
VI2

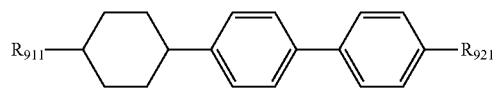
VI3

VI4

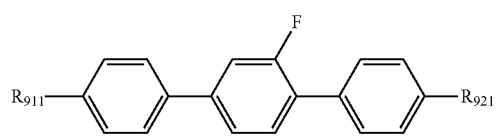
VI5

VI6

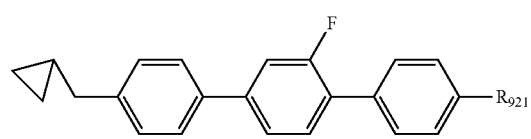
VI7

-continued

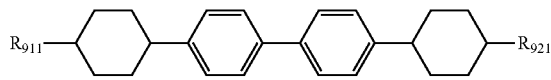
VI8

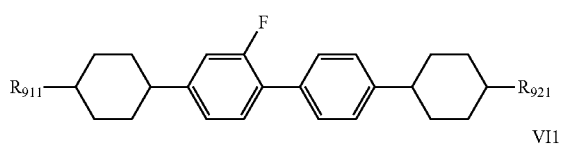
VI9

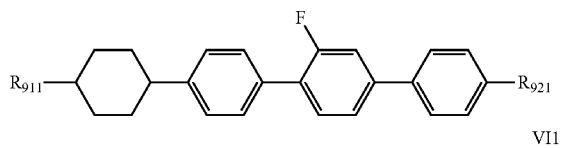
VI10

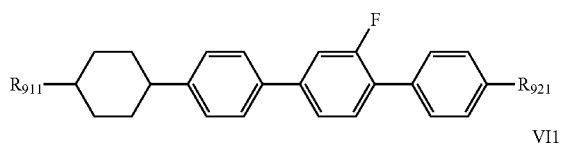
VI11

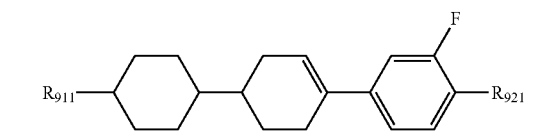
VI12

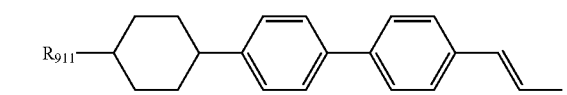
VI13

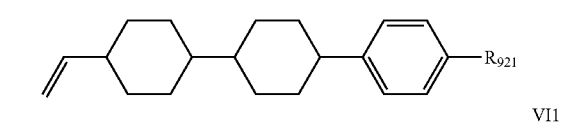
VI14

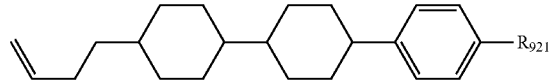
VI15 wherein $R_{911}$ represents an alkyl group having a carbon atom number of 1-5, and $R_{921}$ represents an alkyl group having a carbon atom number of 1-5;

The addition amounts of the single monomers of formulas I, II, III, IV, V, and VI most closely depend on the number of rings, wherein the larger the number of rings, the poorer the solubility in general; and the solubility is also related to the end alkyl chains of a monomer, wherein the solubility of a monomer with alkyl is generally greater than that of a monomer with alkoxy, and by contrast when the carbon atom number is 1-5, the greater the carbon atom number, the better the solubility in general.

Each monomer has a different performance and is used to adjust the various parameters of a liquid crystal, so that the liquid crystal is adaptive the needs of liquid crystal display devices of different specifications.

The liquid crystal composition of the present invention has a good stability against light and heat, a lower viscosity, a wider refractive index that may be achieved by adjustment, and a higher clearing point (a very wide service temperature range), and in particular, the liquid crystal composition has a higher light transmittance, thus allowing a display device to have a higher brightness or an energy saving effect.

Another technical problem to be solved by the present invention is to provide a liquid crystal compound represented by formula I-A,

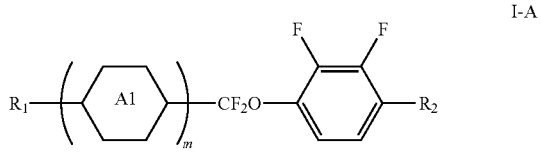
I-A wherein $R_1$ and $R_2$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more non-connected $CH_2$ in $R_0$, $R_1$, $R_2$ and $R_3$ may be substituted with cyclopentyl, cyclobutyl, cyclopropyl, or —O—; m represents one of 1, 2 and 3;

represents one of

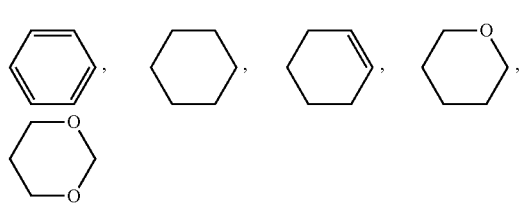

and any fluorobenzene;

The compounds of formula I-A are preferably compounds of formula I1-I3, I5-I8 and I10-I14.

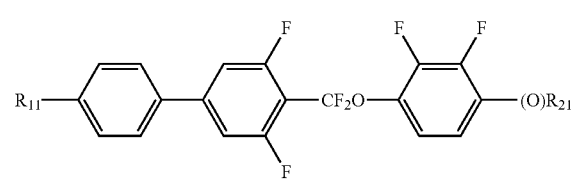
I1

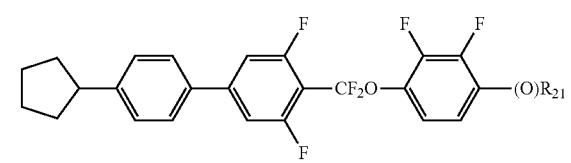
I2

-continued

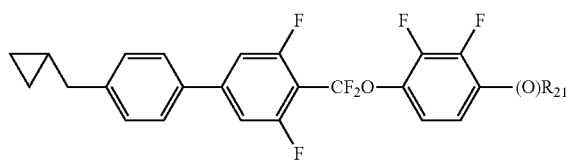
I3

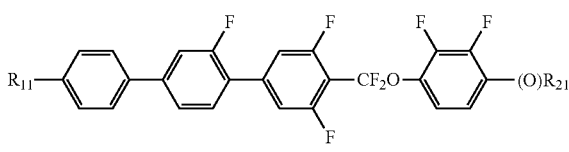
I5

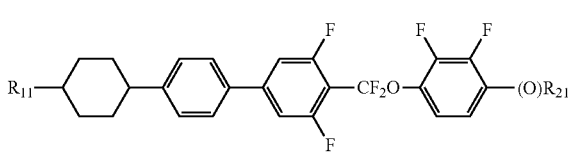
I6

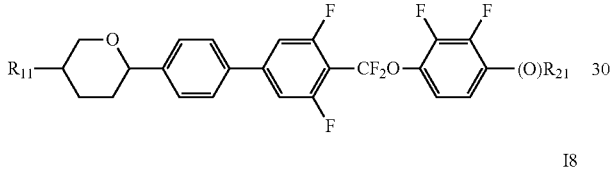
I7

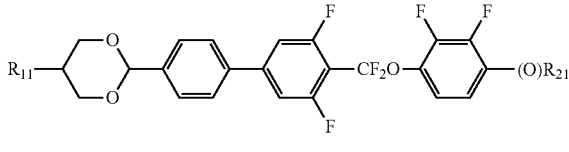
I8

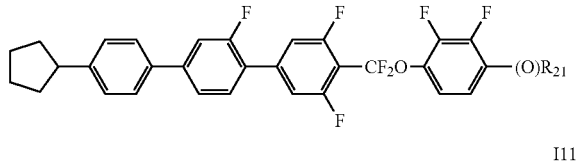
I10

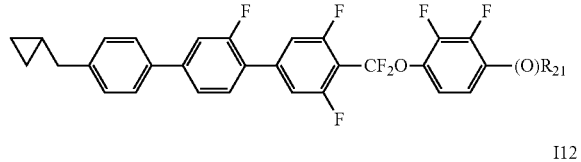
I11

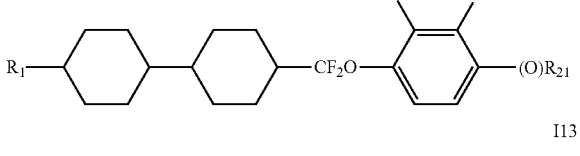
I12

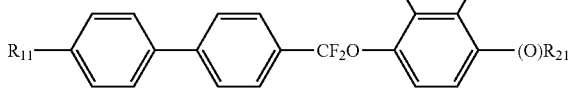
I13

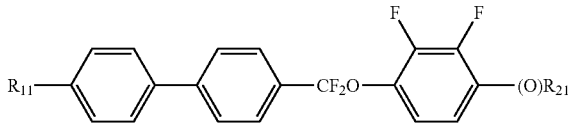

-continued

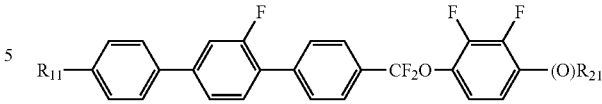
I14 wherein $R_{11}$ represents an alkyl group having a carbon atom number of 1-6, and $R_{21}$ represents an alkyl group having a carbon atom number of 1-5

Synthetic route:

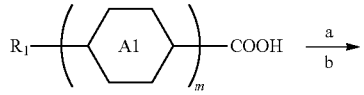

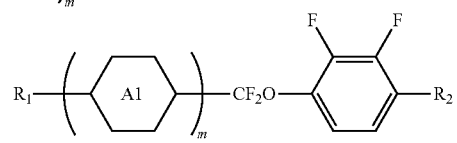

a: 1,3-dimercaptopropane trifluoromethanesulfonic acid 3HF.NEt3 Br2 b:

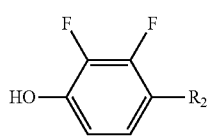

The liquid crystal compounds of formula I-A have a greater dielectric anisotropy in the liquid crystal molecule major axis parallel direction and vertical direction, with the difference (Δε) between the major axis parallel direction dielectric anisotropy and vertical direction dielectric anisotropy being smaller, and the overall anisotropy is close to neutral; furthermore, the liquid crystal compounds have the advantages of a higher clearing point CP, a good stability against light and heat, a greater elastic constant, etc. Moreover, there are a great number of raw material sources, the synthesis is simple, and the cost is lower.

The present invention further relates to a liquid crystal display element or liquid crystal display comprising a compound of formula I-A and a liquid crystal composition formed by the combination of formulas I, II, III, IV, V and VI, and said liquid crystal display element or liquid crystal display is an active matrix display element or display or a passive matrix display element or display.

The display element or display may be of a TN, ECB, VA, IPS, FFS, PS-TN, PS-VA, PS-IPS, PS-FFS, PA-VA, PA-IPS, PA-FFS, PI-less VA, PI-less IPS, or PI-less-FFS LCD mode.

DETAILED DESCRIPTION OF EMBODIMENTS

The present invention is further described as below in combination with particular embodiments, but the present invention is not limited to the following embodiments. Said methods, if not otherwise indicated, are all conventional methods. Said raw materials, if not otherwise indicated, can all be available through public commercial approaches.

The reaction process is generally monitored through TLC, and the post-treatments after the reaction is completed are generally water washing, extracting, combining organic phases and then drying, evaporating and removing the solvent under a reduced pressure, recrystallization and column chromatographic separation; and a person skilled in the art would be able to achieve the present invention according to the following description.

In the present specification, the percentages are mass percentages, the temperatures are in degree Celsius (° C.), and the specific meanings of other symbols and the test conditions are as follows:

Cp represents the clearing point (° C.) of the liquid crystal measured by a DSC quantitative method;

Δn represents the optical anisotropy, $n_o$ is the refractive index of an ordinary light, $n_e$ is the refractive index of an extraordinary light, the test condition is 25±2° C. and 589 nm, and an abbe refractometer is used for the test;

Δε represents the dielectric anisotropy, $\Delta\varepsilon = \varepsilon_\square - \Delta_\square$, wherein $\varepsilon_\square$ is a dielectric constant parallel to a molecular axis, and $\varepsilon_\square$ is a dielectric constant perpendicular to the molecular axis, the test condition is 25±0.5° C., a 20 micron parallel cell is used, and INSTEC: ALCT-IR1 is used for the test;

γ1 represents a rotary viscosity (mPa·s), the test condition is 25±0.5° C., a 20 micron parallel cell is used, and INSTEC: ALCT-IR1 is used for the test; and T (%) represents a transmittance, T (%)=100%*bright state (Vop) luminance/light source luminance, the test device is DMS501, the test condition is 25±0.5° C., the test cell is a 3.3 micron IPS test cell, both the electrode spacing and the electrode width are 10 microns, and the included angle between the frictional direction and the electrode is 10°; therefore, there is a positive correlation between $\varepsilon_\square$ and T, so in the evaluation of the transmittance, $\varepsilon_\square$ can be used as an evaluation index for indication.

In the examples of the present invention application, liquid crystal monomer structures are represented by codes, wherein the code representation of cyclic structures, end groups and linking groups of the liquid crystals are shown in tables (I) and (II) below

TABLE (I)

Codes corresponding to cyclic structures

| Cyclic structure | Corresponding code |
|---|---|
| 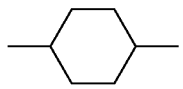 | C |
| 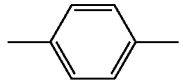 | B |
| 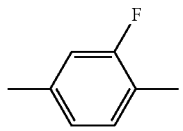 | B(3F) |
| 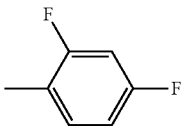 | B(2F,4F) |

TABLE (I)-continued

Codes corresponding to cyclic structures

| Cyclic structure | Corresponding code |
|---|---|
| 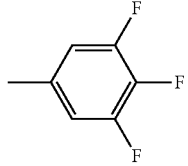 | B(3F,4F,5F) |
|  | B(4F) |
| 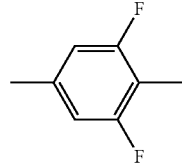 | B(3F,5F) |
| 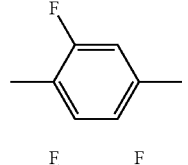 | B(2F) |
| 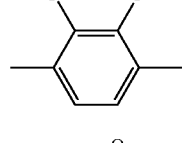 | B(2F,3F) |
| 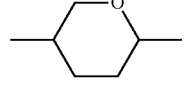 | C[3O] |
| 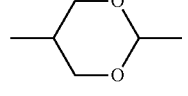 | C[3O,5O] |
| 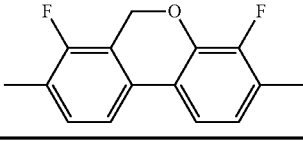 | Sa |

TABLE (II)

Codes corresponding to end groups and linking groups

| End group and linking group | Corresponding code |
|---|---|
| $C_nH_{2n+1}-$ | n |
| $C_nH_{2n+1}O-$ | nO |
| $-OCF_3$ | $OCF_3$ |
| $-CF_2O-$ | $CF_2O$ |
| $-F$ | F |
| $-CH_2CH_2-$ | E |
| $-CH=CH-$ | V |
| $-CH_2O-$ | 1O |
| $-CH=CH-C_nH_{2n+1}$ | Vn |

TABLE (II)-continued

Codes corresponding to end groups and linking groups

| End group and linking group | Corresponding code |
|---|---|
| 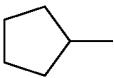 | C(5) |
| 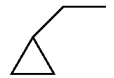 | C(3)1 |

For example:

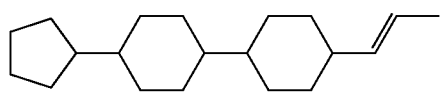 [SMILES: C/C=C/C1CCC(C2CCC(C3CCCC3)CC2)CC1]

C(5)CCV1

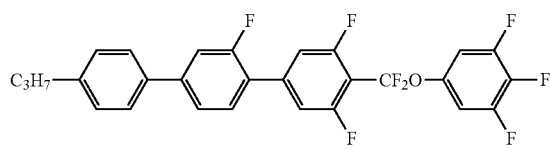

3BB(3F) B(3F,5F)CF2OB(3F,4F,5F)

Example 1

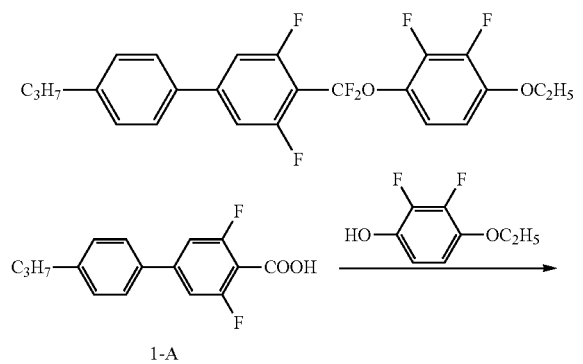

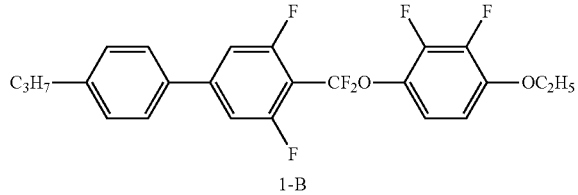

27.6 g of (1-A), 30 ml of toluene and 30 ml of isooctane are added to a 250 ml three-necked flask, followed by the addition of 14 g of 1,3-dimercaptopropane, the suspension described above is heated to 50° C. with stirring, 19.2 g of trifluoromethanesulfonic acid is added within 30 minutes, after the addition, the temperature is raised to reflux, the generated water is separated out, after the water is completely separated out, the suspension is cooled to 90° C., 100 ml of methyl tert-butyl ether is added at 70-90° C. within 45 minutes, the suspension continues to be cooled so as to precipitate a crystal, filtration is carried out under the protection of nitrogen, and the resulting crystal is washed with methyl tert-butyl ether (25 ml×4) followed by vacuum drying to give 45 g of crystal (a dithiane trifluoromethanesulfonate).

A mixed solution of 14.8 g of 3,4,5-trifluorophenol, 10.8 g of triethylamine and 130 ml of dichloromethane is added to a 500 ml three-necked flask and cooled to −70° C., the above-mentioned 45 g of crystal in 120 ml of dichloromethane is added dropwise within 45 minutes and stirred for one hour at this temperature, and then 73.5 ml of NEt$_3$.3HF is added within 5 minutes. Thereafter, 72.7 g of liquid bromine in 30 ml of methylene chloride is added at −70° C. within one hour, then the reaction continues at −70° C. for one hour, the temperature is raised to 0° C., the reaction liquid is poured into 160 ml of a 32% aqueous sodium hydroxide solution and 300 g of ice, and the pH of the reaction liquid is adjusted to 5-8 by means of dropwise adding about 45 g of the 32% aqueous sodium hydroxide solution. After liquid separation, the aqueous phase is extracted with 80 ml of dichloromethane, organic phases are combined, filtered with 4 g of diatomite and washed with water, and the solvent is evaporated to dryness under a reduced pressure. The resulting crude product is subjected to column chromatography followed by recrystallization with petroleum ether to give 21 g of a product (1-B) with GC: 99.92%.

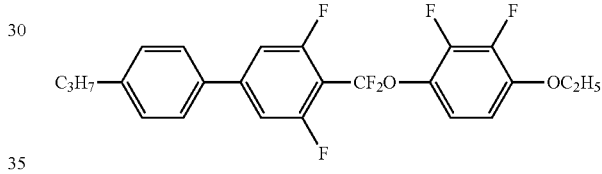

Δε[1 KHz, 20° C.]: −1.0
ε$_⊥$: 8.7
ε$_{//}$: 7.3
Δn[589 nm, 20° C.]: 0.164
Cp: 65° C.

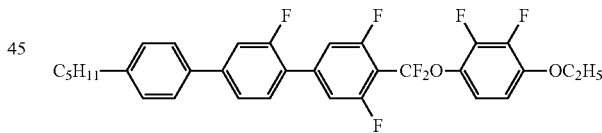

Δε[1 KHz, 20° C.]: 0.3
ε$_⊥$: 8.0
ε$_{//}$: 8.3
Δn[589 nm, 20° C.]: 0.230
Cp: 171° C.

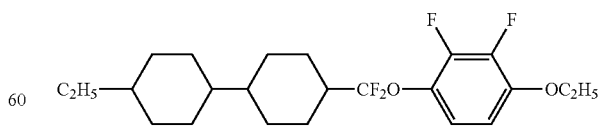

Δε[1 KHz, 20° C.]: −3.9
ε$_⊥$: 8.5
ε$_{//}$: 4.4
Δn[589 nm, 20° C.]: 0.086
Cp: 126° C.

Example 2

| Classification | Liquid crystal monomer code | Content (%) |
| --- | --- | --- |
| II-B | 3CCV | 60 |
| I | 3C[3O,5O]B(3F,5F)CF2OB(2F,3F,4O2) | 8 |
| I | 5B B(3F,5F)CF2OB(2F,3F,4O3) | 9 |
| I | 3CCCF2OB(2F,3F,4O4) | 6 |
| I | 3C[3O,5O]BB(3F,5F)CF2OB(2F,3F,4O2) | 7 |
| I | 5C[3O,5O]B(3F,5F)CF2OB(2F,3F,4O3) | 2 |
| I | 4BB(3F)B(3F,5F)CF2OB(2F,3F,4O2) | 8 |

$\Delta\epsilon$[1 KHz, 20° C.]: 1.2
$\epsilon_\square$: 4.1
$\Delta$n[589 nm, 20° C.]: 0.104
Cp: 96° C.
$\gamma_1$: 88 mPa · s.

Example 3

| Classification | Liquid crystal monomer code | Content (%) |
| --- | --- | --- |
| II-B | 3CCV | 33 |
| II | 3CC2 | 4 |
| II | 3CBO2 | 3 |
| II | 3CC5 | 6 |
| I | 3BB(3F,5F)CF2OB(2F,3F,4O2) | 7.5 |
| VI | 3CBB2 | 4 |
| V | C(5)1OSaO4 | 6 |
| IV | 2OB B(2F,3F)O4 | 4.5 |
| IV | 3CC1OB(2F,3F)O2 | 12 |
| IV | 3C1OB(2F,3F)O2 | 5 |
| IV | 2CC1OB(2F,3F)O2 | 11 |
| IV | 4CC1OB(2F,3F)O2 | 4 |

$\Delta\epsilon$[1 KHz, 20° C.]: −3.71
$\epsilon_\square$: 7.7
$\Delta$n[589 nm, 20° C.]: 0.088
Cp: 76° C.
$\gamma_1$: 112 mPa · s.

Comparative Example 1

| Classification | Liquid crystal monomer code | Content (%) |
| --- | --- | --- |
| II-B | 3CCV | 33 |
| II | 3CC2 | 4 |
| II | 3CBO2 | 5 |
| II | 3CC5 | 6 |
| VI | 3CBB2 | 8 |
| V | C(5)1OSaO4 | 6 |
| IV | 2OB B(2F,3F)O4 | 5 |
| IV | 2OB B(2F,3F)O2 | 3 |
| IV | 3CC1OB(2F,3F)O2 | 12 |
| IV | 3C1OB(2F,3F)O2 | 5 |
| IV | 2CC1OB(2F,3F)O2 | 11 |
| IV | 4CC1OB(2F,3F)O2 | 2 |

$\Delta\epsilon$[1 KHz, 20° C.]: −3.50
$\epsilon_\square$: 7.14
$\Delta$n[589 nm, 20° C.]: 0.091
Cp: 76° C.
$\gamma_1$: 96 mPa · s.

Suitable for negative IPS and VA mode displays.

Comparative Example 1 does not contain any component of formula I, and comparing Example 3 with Comparative Example 1, the addition of the component of formula I enables an obvious increase of $\epsilon_\square$. Upon transmittance testing, the transmittance of Example 3 is higher than that of Comparative Example 1 by 5%.

Example 4

| Classification | Liquid crystal monomer code | Content (%) |
| --- | --- | --- |
| II-B | 3CCV | 46 |
| II | 5BBO2 | 4 |
| II | 3CCV1 | 6 |
| VI | VCCB1 | 12 |
| VI | 3CCB3 | 7 |
| I | 3B B(3F,5F)CF2OB(2F,3F,4O2) | 8 |
| III | 3CCBB(3F,4F) | 1 |
| III | 3BBB(2F,4F) | 4 |
| III | C(5)BB(3F)B(3F,5F)CF2OB(3F,4F,5F) | 5.5 |
| III | C(5)CBB(3F,5F)CF2OB(3F,4F,5F) | 5 |
| III | C(5)BBB(3F) B(3F,4F,5F) | 1.5 |

$\Delta\epsilon$[1 KHz, 20° C.]: 2.76
$\epsilon_\square$: 2.98
$\Delta$n[589 nm, 20° C.]: 0.0986
Cp: 84° C.
$\gamma_1$: 58 mPa · s.

Example 4 is particularly suitable for positive, high transmittance TV-IPS mode liquid crystals.

Example 5

| Classification | Liquid crystal monomer code | Content (%) |
| --- | --- | --- |
| II-B | 3CCV | 40 |
| II | 5BBO2 | 7 |
| II | 3CCV1 | 7 |
| VI | VCCB1 | 13 |
| VI | 3CCB3 | 6 |
| I | 3B B(3F,5F)CF2OB(2F,3F,4O2) | 10 |
| III | 3CCBB(3F,4F) | 2 |
| III | 3CCB(4F) | 3 |
| III | C(3)1BB(3F)B(3F,5F)CF2OB(3F,4F,5F) | 4 |
| III | C(5)CBB(3F,5F)CF2OB(3F,4F,5F) | 3 |
| III | C(5)C[3O]BB(3F,5F)CF2OB(3F,4F,5F) | 4 |
| III | C(5)BBB(3F) B(3F,4F,5F) | 1 |

$\Delta\epsilon$[1 KHz, 20° C.]: 2.89
$\epsilon_\square$: 3.13
$\Delta$n[589 nm, 20° C.]: 0.0988
Cp: 87° C.
$\gamma_1$: 67 mPa · s.

Example 5 is particularly suitable for positive, high transmittance TV-IPS mode liquid crystals.

Comparative Example 2

The liquid crystal composition obtained by removing 10% of the component I from Example 5 is the liquid crystal composition of Comparative Example 2, and upon transmittance testing, the transmittance of Example 5 is higher than that of Comparative Example 2 by 6%.

Example 6

| Classification | Liquid crystal monomer code | Content (%) |
| --- | --- | --- |
| II-B | 3CCV | 38.5 |
| II | 3CCV1 | 10.5 |
| I | 3B B(3F,5F)CF2OB(2F,3F,4O2) | 10 |
| VI | VCCB1 | 2.75 |
| VI | V2CCB1 | 4 |
| VI | 3CBBV1 | 4 |

-continued

| Classification | Liquid crystal monomer code | Content (%) |
|---|---|---|
| III | 2BBB(2F,4F) | 3.5 |
| III | 5BBB(2F,4F) | 3 |
| III | C(5)BB(3F)B(3F,5F)CF2OB(3F,4F,5F) | 4 |
| III | C(5)BB(3F,5F)CF2OB(3F,4F,5F) | 9.75 |
| III | C(5)BB(3F)B(3F,4F,5F) | 5 |
| III | C(5)CBB(3F,5F)CF2OB(3F,4F,5F) | 5 |

Δε[1 KHz, 20° C.]: 5.27
ε∏: 3.47
Δn[589 nm, 20° C.]: 0.1129
Cp: 76.5° C.
γ₁: 62 mPa · s.

Example 7

| Classification | Liquid crystal monomer code | Content (%) |
|---|---|---|
| II-B | 3CCV | 18.5 |
| II | 3CCV1 | 10.5 |
| I | 3B B(3F,5F)CF2OB(2F,3F,4O2) | 10 |
| VI | VCCB1 | 12.75 |
| VI | V2CCB1 | 4 |
| VI | 3CBBV1 | 14 |
| III | 2BBB(2F,4F) | 3.5 |
| III | 5BBB(2F,4F) | 3 |
| III | C(5)BB(3F)B(3F,5F)CF2OB(3F,4F,5F) | 4 |
| III | C(5)BB(3F,5F)CF2OB(3F,4F,5F) | 9.75 |
| III | C(5)BB(3F)B(3F,4F,5F) | 5 |
| III | C(5)CBB(3F,5F)CF2OB(3F,4F,5F) | 5 |

Δε[1 KHz, 20° C.]: 5.37
ε∏: 3.49
Δn[589 nm, 20° C.]: 0.1139
Cp: 88.5° C.
γ₁: 69 mPa · s.

Suitable for positive TN and IPS mode displays.

The liquid crystal composition of the present invention has a good stability against light and heat, a lower viscosity, a wider refractive index that may be achieved by adjustment, and a higher clearing point (a very wide service temperature range), and in particular, the liquid crystal composition has a higher light transmittance, thus allowing a display device to have a higher brightness or an energy saving effect.

The invention claimed is:

1. A liquid crystal composition, comprising one or more compounds of formula I and further comprising one or two compounds of formula II-B,

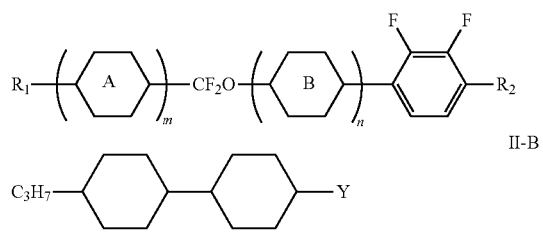

wherein $R_1$, and $R_2$ each independently represent an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more nonadjacent —$CH_2$— in $R_1$, and $R_2$ may be substituted with cyclopentylene group, cyclobutylene group, cyclopropylene group or —O—; Y represents ethyl or ethenyl;

each independently represent one of

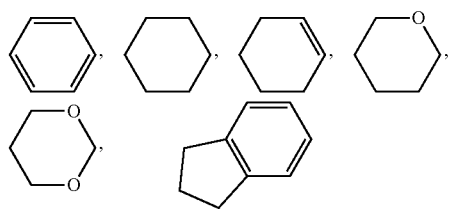

and any fluorobenzene;

represents benzene or fluorobenzene; and m represents one of 1, 2 and 3, and n represents one of 1 and 0.

2. The liquid crystal composition according to claim 1, wherein said one or more compounds represented by formula I are one or more of compounds represented by formulas I1 to I14; said one or more compounds represented by formula II-B are one or two of compounds represented by formulas II-B-1 and II-B-2,

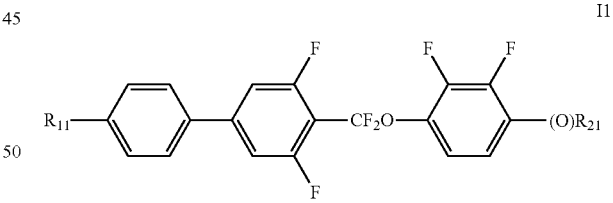

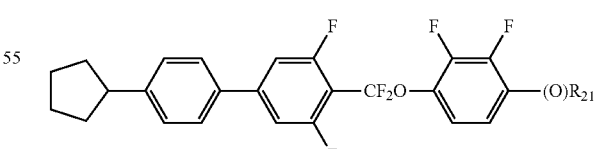

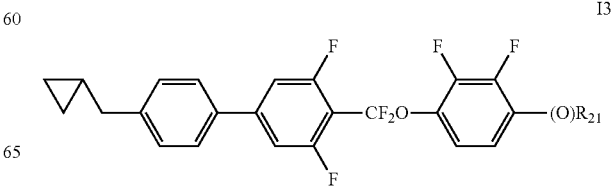

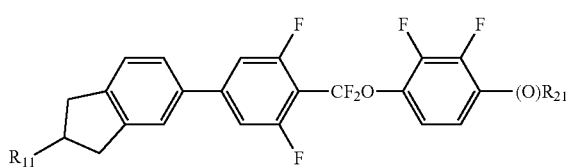
I4

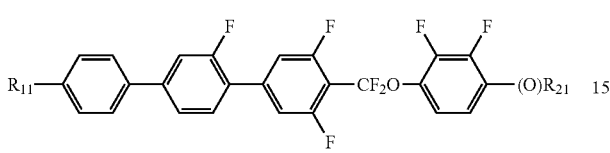
I5

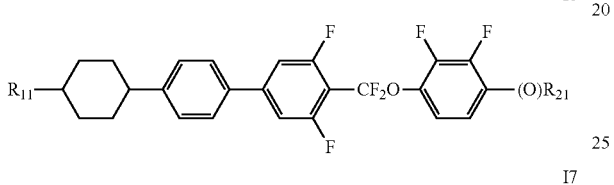
I6

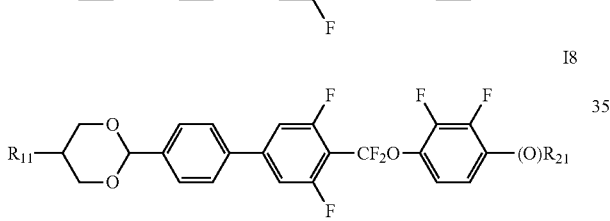
I7

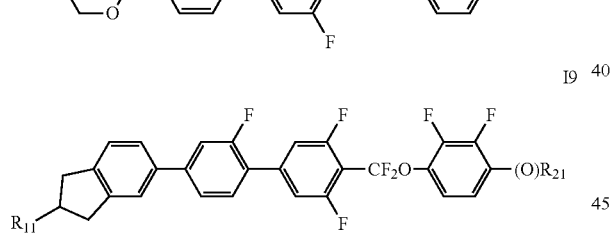
I8

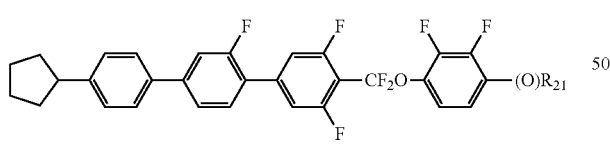
I9

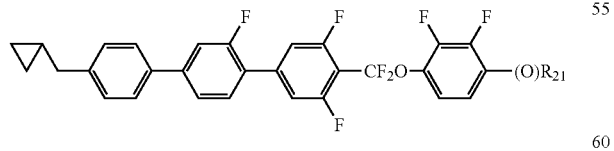
I10

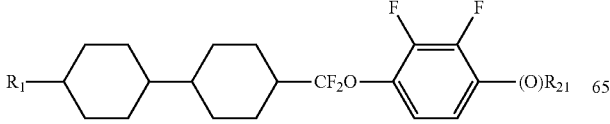
I11

I12

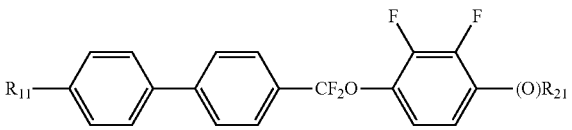
I13

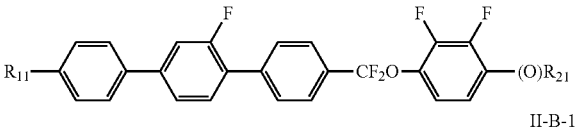
I14

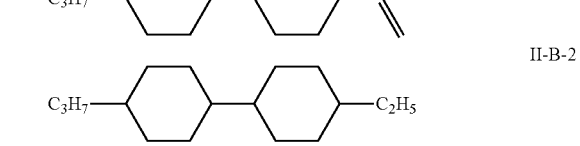
II-B-1

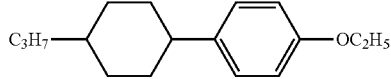
II-B-2

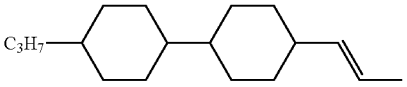

wherein $R_{11}$ represents an alkyl group having a carbon atom number of 1-6, and $R_{21}$ represents an alkyl group having a carbon atom number of 1-5.

3. The liquid crystal composition according to claim 1, wherein in said liquid crystal composition, the content in mass percentage of the compounds represented by formula I is 1-40%, the content in mass percentage of formula II-B is 5-60%, and, said liquid crystal composition further comprises one or more compounds represented by formulas II-1 to II-13, the content in mass percentage of one or more compounds represented by formulas II-1 to II-13 is no more than 50%,

II-1

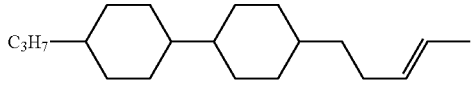

II-2

II-3

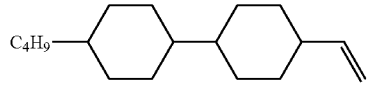

II-4

II-5

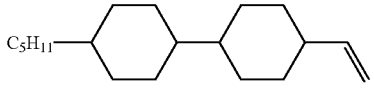

II-6

II-7

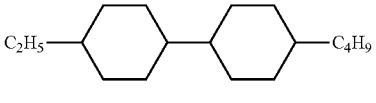

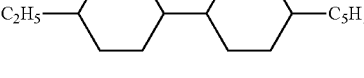

-continued

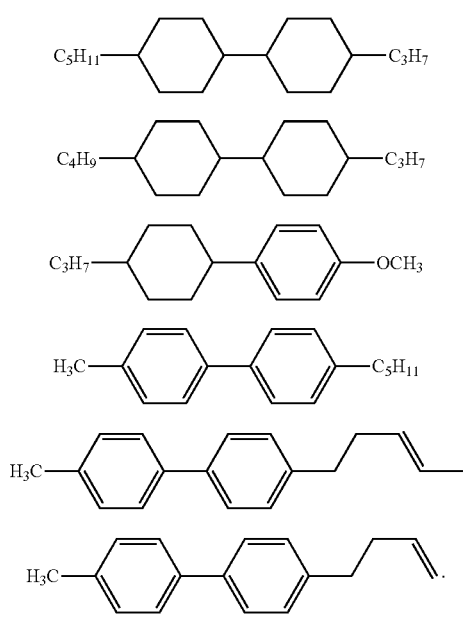

II-8
II-9
II-10
II-11
II-12
II-13

4. The liquid crystal composition according to claim 1, wherein said liquid crystal composition is a positive liquid crystal composition, and said liquid crystal composition further comprises one or more compounds represented by formula III

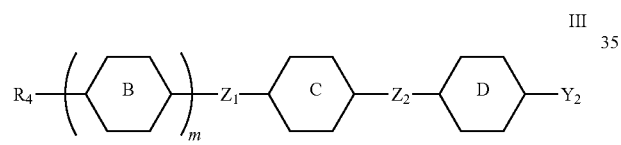

III wherein $R_4$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more —$CH_2$— in $R_4$ may be substituted with cyclopentylene group, cyclobutylene group, cyclopropylene group;

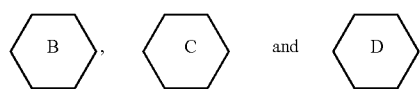

each independently represents one of:

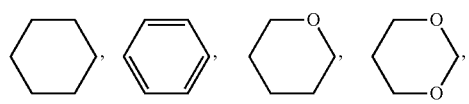

-continued

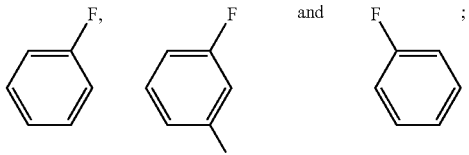

m represents one of 1, 2 and 3; $Z_1$ and $Z_2$ each independently represent a single bond, —$CF_2O$—, —$CH_2CH_2$—, or —$CH_2O$—; and $Y_2$ represents F, a fluoro-substituted alkyl group having a carbon atom number of 1-5, a fluoro-substituted alkoxy group having a carbon atom number of 1-5, a fluoro-substituted alkenyl group having a carbon atom number of 2-5, or a fluoro-substituted alkenoxy group having a carbon atom number of 3-8.

5. The liquid crystal composition according to claim 4, wherein said one or more compounds represented by formula III are compounds of formula III1 to III22

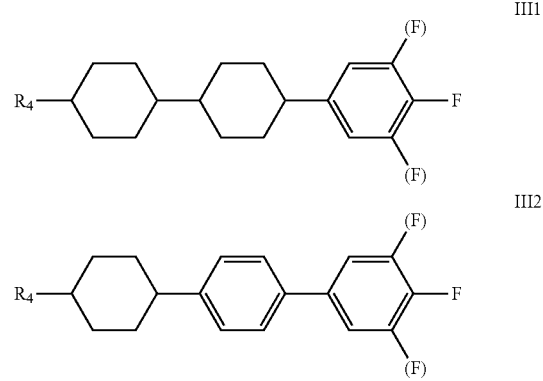

III1
III2
III3
III4

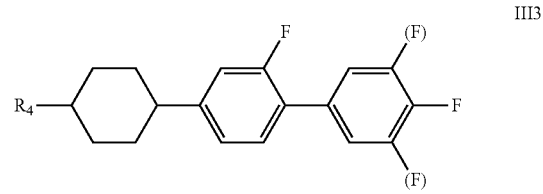

III5

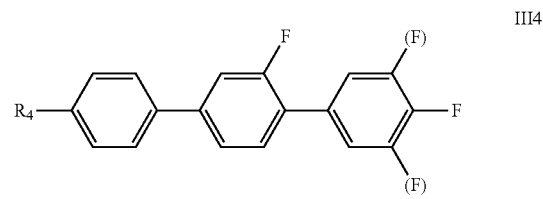

III6

-continued

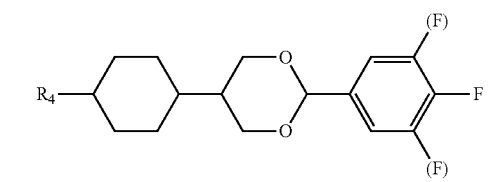
III7

III8

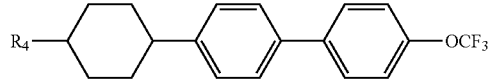
III9

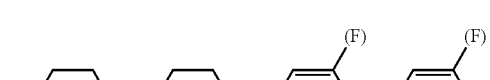
III10

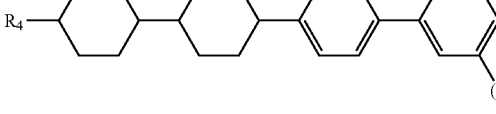
III11

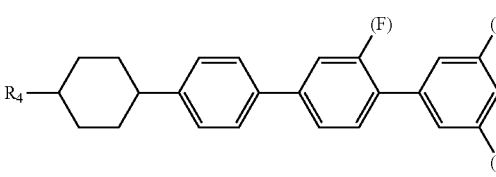
III12

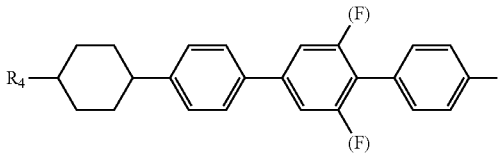
III13

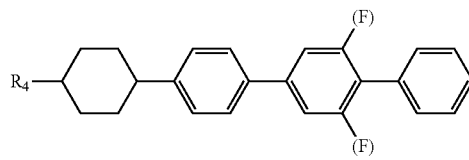
III14

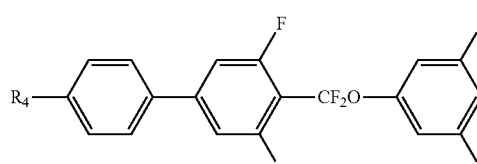
III15

-continued

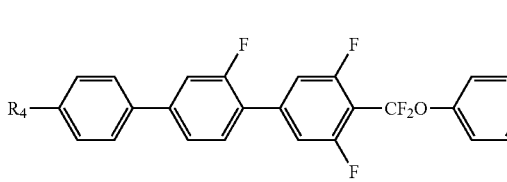
III16

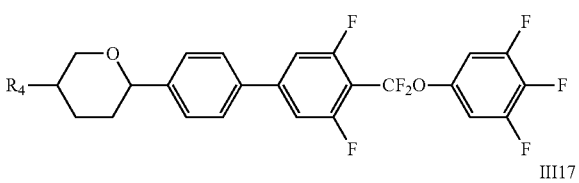
III17

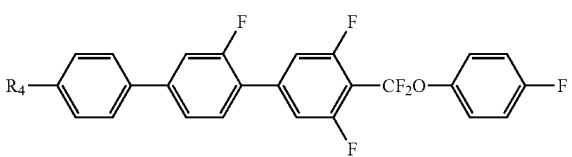
III18

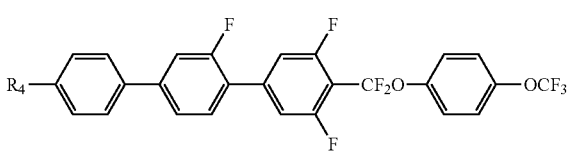
III19

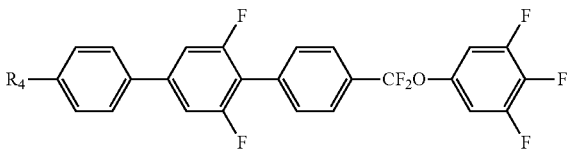
III20

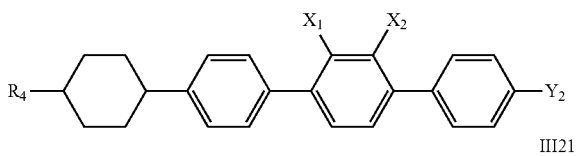
III21

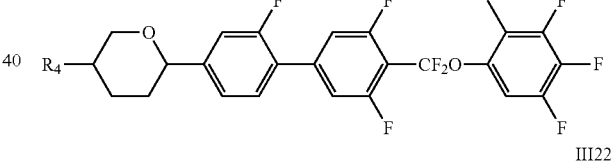
III22

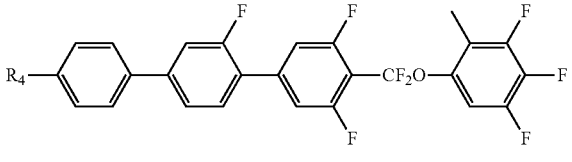

wherein $X_1$ and $X_2$ each independently represent H or F;
wherein $R_4$ represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any $CH_2$ in $R_4$ may be substituted with cyclopentylene group, cyclobutylene group, cyclopropylene group; (F) represents H or F; and
$Y_2$ represents F, a fluoro-substituted alkyl group having a carbon atom number of 1-5, a fluoro-substituted alkoxy group having a carbon atom number of 1-5, a fluoro-substituted alkenyl group having a carbon atom number of 2-5, or a fluoro-substituted alkenoxy group having a carbon atom number of 3-8.

6. The liquid crystal composition according to claim 1, wherein said liquid crystal composition is a negative liquid crystal composition, and said liquid crystal composition further comprises one or more compounds represented by formula IV

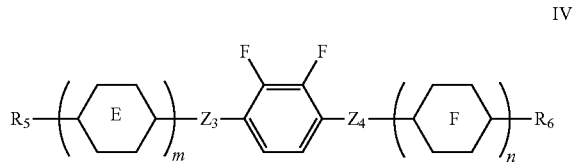

IV wherein $R_5$ and $R_6$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any —$CH_2$— in $R_5$ and $R_6$ may be substituted with cyclopentylene group, cyclobutylene group, cyclopropylene group;

$Z_3$ and $Z_4$ each independently represent a single bond, —$CH_2CH_2$— or —$CH_2O$—; and

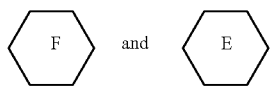

each independently represent one of

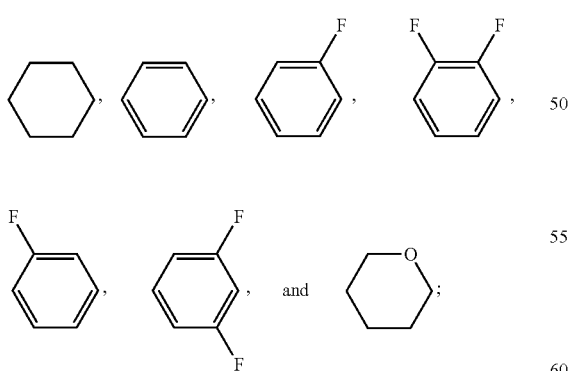

and m represents one of 1, 2 and 3, and n represents one of 0 and 1.

7. The liquid crystal composition according to claim 6, wherein said one or more compounds represented by formula IV are one or more compound of formula IV1 to IV11:

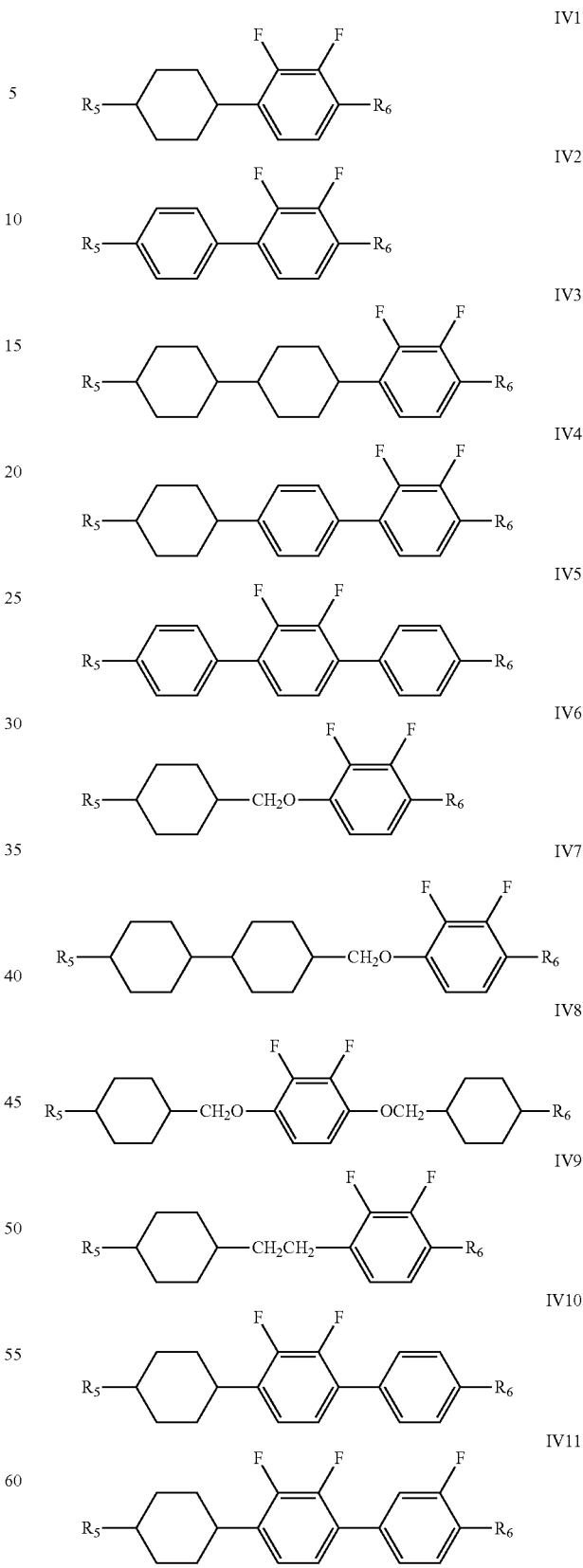

wherein $R_5$ and $R_6$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and —CH$_2$— in R$_5$ and R$_6$ may be substituted with cyclopentylene group, cyclobutylene group, cyclopropylene group.

8. The liquid crystal composition according to claim 1, wherein said liquid crystal composition is a negative liquid crystal composition, and said liquid crystal composition further comprises one or more compounds represented by formula V

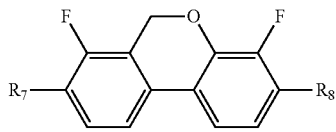

V wherein R$_7$ and R$_8$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any —CH$_2$— in R$_7$ and R$_8$ may be substituted with cyclopentylene group, cyclobutylene group, cyclopropylene group.

9. The liquid crystal composition according to claim 1, wherein said liquid crystal composition may further comprise a compound of formula VI

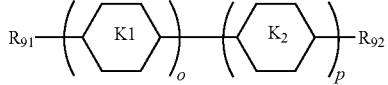

VI wherein R$_{91}$ represents an alkyl group having a carbon atom number of 1-5 or an alkenyl group having a carbon atom number of 2-5; R$_{92}$ represents an alkyl group having a carbon atom number of 1-5, an alkoxy group having a carbon atom number of 1-5, or an alkenyl group having a carbon atom number of 2-5, and any —CH$_2$— in R$_{91}$ and R$_{92}$ may be substituted with cyclopentylene group, cyclobutylene group, cyclopropylene group; o and p represent one of 1 and 2; and

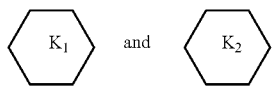

each independently represent one of

and any fluorobenzene.

10. A liquid crystal compound represented by formula I-A,

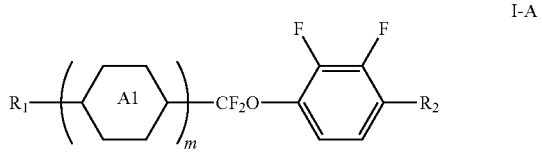

I-A wherein R$_1$ and R$_2$ each independently represents an alkyl group having a carbon atom number of 1-10, a fluoro-substituted alkyl group having a carbon atom number of 1-10, an alkoxy group having a carbon atom number of 1-10, a fluoro-substituted alkoxy group having a carbon atom number of 1-10, an alkenyl group having a carbon atom number of 2-10, a fluoro-substituted alkenyl group having a carbon atom number of 2-10, an alkenoxy group having a carbon atom number of 3-8 or a fluoro-substituted alkenoxy group having a carbon atom number of 3-8, and any one or more nonadjacent —CH$_2$— in R$_1$, and R$_2$ may be substituted with cyclopentylene group, cyclobutylene group, cyclopropylene group, or —O—; m represents one of 1, 2 and 3;

represents one of

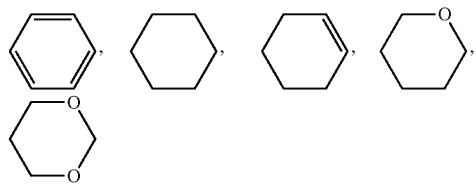

and any fluorobenzene.

11. The liquid crystal composition represented by formula I-A according to claim 10, wherein said one or more compounds represented by formula I-A are one or more compound of formulas I1-I3, I5-I8, and I10-I14:

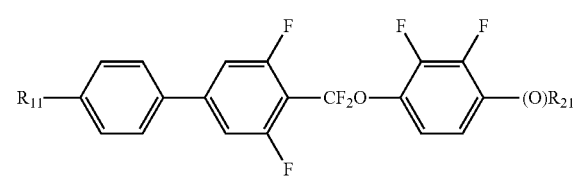

I1

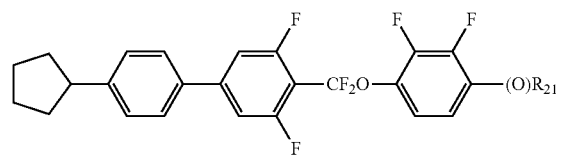
I2
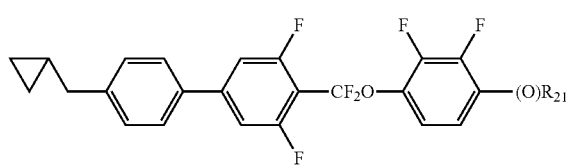
I3
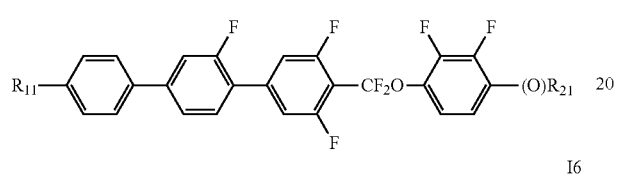
I5
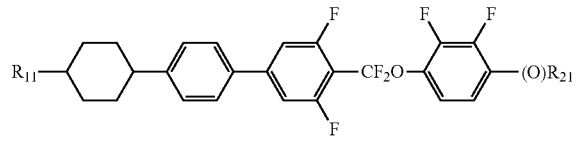
I6
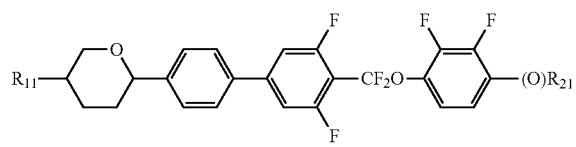
I7
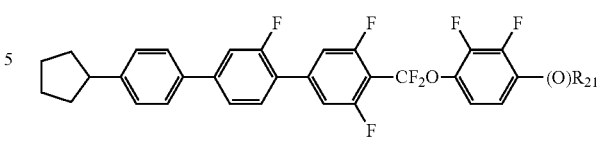
I10
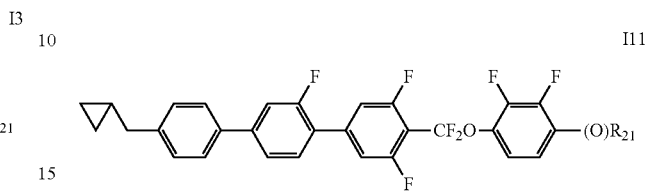
I11
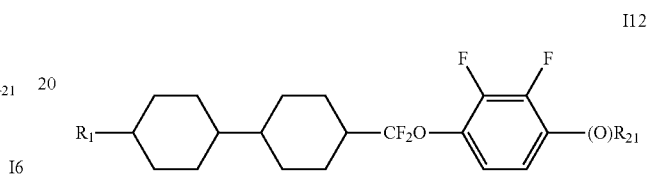
I12
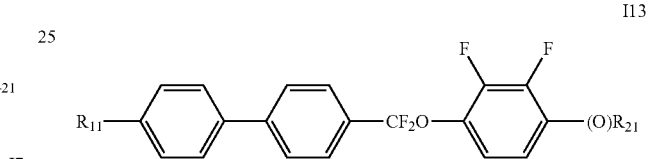
I13
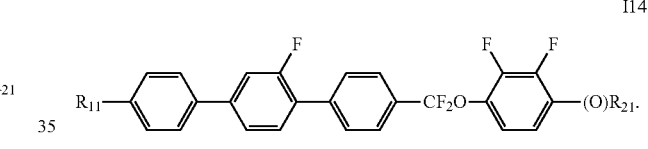
I14
12. A liquid crystal display element or liquid crystal display comprising the liquid crystal composition of claim 1, wherein said liquid crystal display element or liquid crystal display is an active matrix display element or display or a passive matrix display element or display.
* * * * *